(12) United States Patent
Lin

(10) Patent No.: US 6,644,970 B1
(45) Date of Patent: Nov. 11, 2003

(54) GUM ADJUSTING AND SHAPING DEVICE

(76) Inventor: Fu Yi Lin, No. 34, Alley43, Lane 123, Sec. 6, Minchi-uan, E. Rd., Neihu Chiu, Taipei (TW)

( * ) Notice: Subject to any disclaimer, the term of this patent is extended or adjusted under 35 U.S.C. 154(b) by 0 days.

(21) Appl. No.: 10/127,540

(22) Filed: Apr. 23, 2002

(51) Int. Cl.[7] .................................................. A61C 8/00
(52) U.S. Cl. ...................................................... 433/173
(58) Field of Search ................................ 433/173, 172, 433/174, 214

(56) References Cited

U.S. PATENT DOCUMENTS

| | | | | |
|---|---|---|---|---|
| 5,110,292 A | * | 5/1992 | Balfour et al. | 433/173 |
| 6,159,010 A | * | 12/2000 | Rogers et al. | 433/172 |
| 6,508,650 B2 | * | 1/2003 | Gittleman | 433/172 |
| 6,540,514 B1 | * | 4/2003 | Falk et al. | 433/173 |

* cited by examiner

Primary Examiner—Kevin Shaver
Assistant Examiner—Melba Bumgarner

(57) ABSTRACT

A gum adjusting and shaping device mainly includes an outer die, an abutments of implanted tooth detachably put in the outer die, and a cap screw received in the abutments of implanted tooth for fixing the latter and the outer die to an artificial implant previously implanted in the tooth socket bone. The outer die is a cylindrical member having a rear end in the form of a truncated cone and can therefore advantageously expand the gum surrounding an empty tooth socket to where an artificial tooth is to be mounted. The expanded gum allows subsequent formation of a tooth mold deeply reaching the root of the abutments of implanted tooth to produce a desired artificial tooth completely matching with neighboring teeth.

3 Claims, 9 Drawing Sheets

GUM ADJUSTING AND SHAPING DEVICE

BACKGROUND OF THE INVENTION

The present invention relates to a gum adjusting and shaping device, and more particularly to a gum shaping device that advantageously creates space between abutment of implants and gum tissue for impression, so that an esthetic artificial tooth can be made easily with deep impression of abutment.

Ideal restoration is particularly important in today's society to replace lost teeth. People feel uncomfortable when nerves in an empty tooth socket are shown, which look ugly. Moreover, the empty tooth socket has an adverse influence on clear articulation. To maintain conveniences in eating, and to maintain a pleasant appearance, it is necessary to mount an artificial tooth to fill up the empty tooth socket.

Conventionally, a gum adjusting and shaping device having a gum-healing cap is used in the process of making a tooth mold and producing and mounting a desired artificial tooth. FIGS. 1 to 9 illustrate in details the steps of mounting the conventional gum adjusting and shaping device for implanting an artificial tooth. In these steps, an artificial implant 4 having a head forming a screw cavity 41 and a body forming a threaded rod 42 are provided. A gum-healing cap 5 in the form of a truncated cone is Provided, which has a threaded rod 51 provided at a rear end thereof for screwing into the screw cavity 41 of the artificial implant 4. An abutment of implanted tooth 6 is Provided, which defines a hollow inner space and has front and rear portions in the form of truncated cones. A screw 61 is received in the inner space of the abutment of implanted tooth 6

First, the gum 2 surrounding the empty tooth socket of an extracted tooth 1 is incised to expose a part of a socket bone 3 above the empty tooth socket. A hole is drilled in the tooth socket bone 3 with a special drill for the artificial implant 4 to implant therein. The artificial implant 4 is implanted in the tooth socket bone 3, with the screw cavity 41 at its head located at an opening of the drilled hole to facilitate performance of subsequent steps. The gum 2 is then sutured, as shown in FIG. 1. After a period of time, the socket bone 3 will adapt itself to and unite with the implanted artificial implant 4. After the artificial implant 4 has united with the socket bone 3, the healed gum 2 is incised again to connect the gum-healing cap 5 to the previously implanted artificial implant 4 by screwing the threaded rod 51 at the rear end of the gum-healing cap 5 into the screw cavity 41 of the artificial implant 4, as shown in FIG. 2. The purpose of screwing the gum-healing cap 5 to the artificial implant 4 is to expand the gum 2 open so that the gum 2 is shaped into a substantially conic cavity. For this purpose, the gum-healing cap 5 must not be removed from the artificial implant 4 until at least one week later. After removal of the gum-healing cap 5 from the artificial implant 4, the abutment of implanted tooth 6 is immediately fixed to,the screw cavity 41 of the artificial implant 4 to substitute for the gum-healing cap 5, as shown in FIGS. 3 and 4.

After the screw 61 in the abutment of implanted tooth 6 is screwed into the screw cavity 41 of the artificial implant 4, an impression tray with material 7 is used to take an accurate contour of the empty tooth socket for making a tooth mold, as shown in FIG. 5. Before taking the accurate contour of the empty tooth socket, the inner space of the abutment of implanted tooth 6 must be filled with filler 62 to ensure that a desired artificial tooth 8 could be produced later to tightly fit on the abutment of implanted tooth 6. After removal of the impression tray with material 7 from the empty tooth socket, production of the desired artificial tooth 8 could be immediately started with a user-specified material. Since it takes a period of time to produce the desired artificial tooth 8, it is necessary to mount a temporary artificial tooth 9 on the abutments of implanted tooth 6 with bonding agent to substitute for the desired artificial tooth 8 during the waiting time, as shown in FIGS. 6 and 7. When the desired artificial tooth 8 is completed, the temporary artificial tooth 9 is removed from the abutment of implanted tooth 6 and the desired artificial tooth 8 is connected to the abutment of implanted tooth 6 by means of bonding agent, as shown in FIGS. 8 and 9.

The above-described steps of mounting a conventional gum adjusting and shaping device for implanting an artificial tooth have the following disadvantages:

1. The gum-healing cap 5 is connected to the artificial implant 4 by screwing the threaded rod 51 into the screw cavity 41, so that the incised gum 2 is shaped around the gum-healing cap 5 during the process of healing. When the incised gum 2 is healed, the gum-healing cap 5 is removed from the empty tooth socket and the abutment of implanted tooth 6 is immediatly mounted. Since the gum 2 will automatically collapse within one or two minutes, it is difficult to keep the gum 2 in the shape obtained from the gum-healing cap 5.

2. Since the gum-healing cap 5 forms only a considerably small cavity at the gum 2, it is not easy for the impression tray with material 7 to fully reach a root portion of the abutment of implanted tooth 6. That is, the temporary artificial tooth 9 and the desired final artificial tooth 8 produced based on the impression tray with material 7 are slightly shorter than a length of the extracted tooth 1. Thus, the desired artificial tooth 8 will mismatch with other neighboring teeth 1 after it is implanted in the empty tooth socket and looks ugly.

3. The gum-healing cap 5 is precision made of an alloy and therefore has a high manufacturing cost.

4. The gum-healing cap 5 is utilized to create space in and shape the gum 2 into a desired configuration. For this purpose, the gum-healing cap 5 must be mounted in the empty tooth socket for a prolonged time to obtain a shaped gum 2. This will inevitably extend the time to carry out the steps of implanting the artificial tooth 8.

It is therefore an object of the inventor to develop an improved gum adjusting and shaping device to facilitate the expansion and shaping of gum and the subsequent formation of accurate tooth mold and desired artificial tooth.

SUMMARY OF THE INVENTION

A primary object of the present invention is to provide a gum adjusting and shaping device that facilitates the expansion and shaping of gum around an extracted tooth and the subsequent formation of accurate tooth mold and desired artificial tooth based on the well-shaped gum.

Another object of the present invention is to provide a gum adjusting and shaping device that omits the conventional gum-healing cap to reduce the time needed to carry out the implantation of an artificial tooth.

A further object of the present invention is to provide a gum adjusting and shaping device that may be easily manufactured at reduced cost and clinical time.

To achieve the above and other objects, the gum adjusting and shaping device of the present invention mainly includes an outer die, an abutment of implanted tooth detachably put in the outer die, and a cap screw received in the abutment of implanted tooth for fixing the latter and the outer die to an artificial implant previously implanted in the tooth socket bone. The outer die is a cylindrical member having a rear end facing the socket bone in the form of a truncated cone and can therefore advantageously expand the gum surrounding an empty tooth socket to where an artificial tooth is to be mounted. The expanded gum allows subsequent formation of a tooth mold deeply reaching the root of the abutment of implanted tooth to produce a desired artificial tooth completely matching with neighboring teeth.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
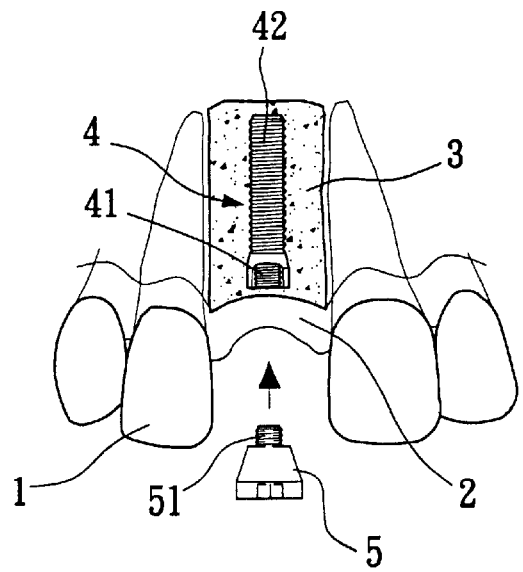
FIG. 1 shows a first step of mounting a conventional gum adjusting and shaping device for implanting an artificial tooth.
Figure 2:
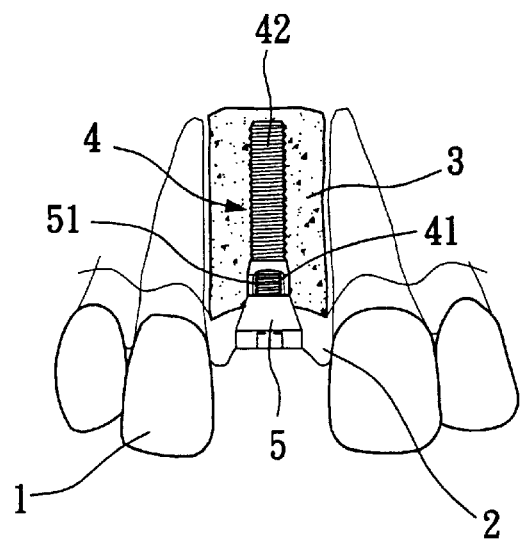
FIG. 2 shows a second step of mounting the conventional gum adjusting and shaping device for implanting an artificial tooth.
Figure 3:
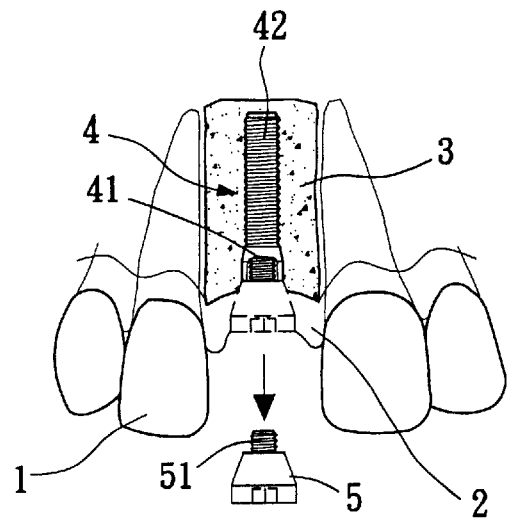
FIG. 3 shows a third step of mounting the conventional gum adjusting and shaping device for implanting an artificial tooth.
Figure 4:
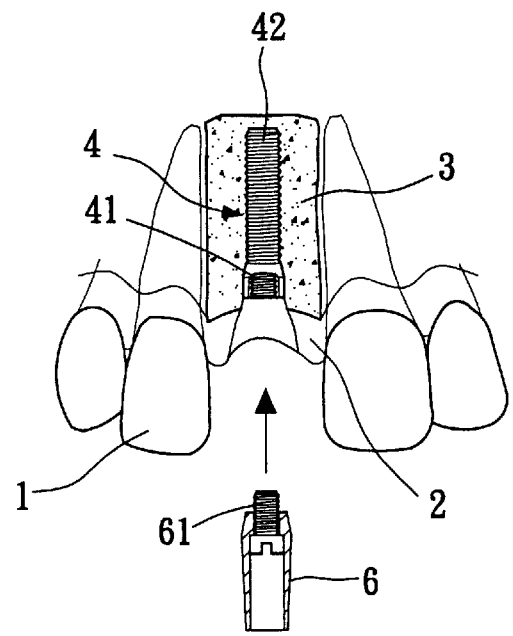
FIG. 4 shows a fourth step of mounting the conventional gum adjusting and shaping device for implanting an artificial tooth.
Figure 5:
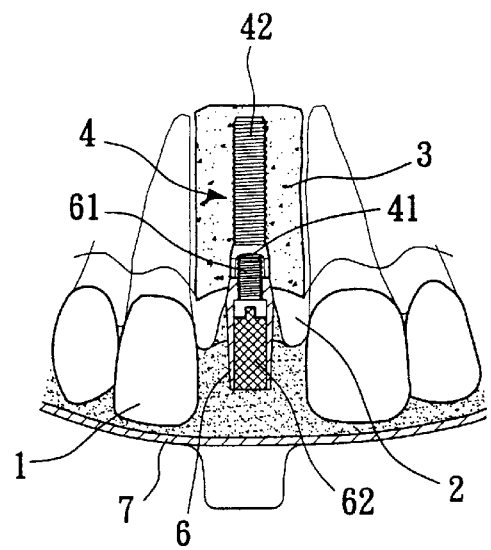
FIG. 5 shows a fifth step of mounting the conventional gum adjusting and shaping device for implanting an artificial tooth.
Figure 6:
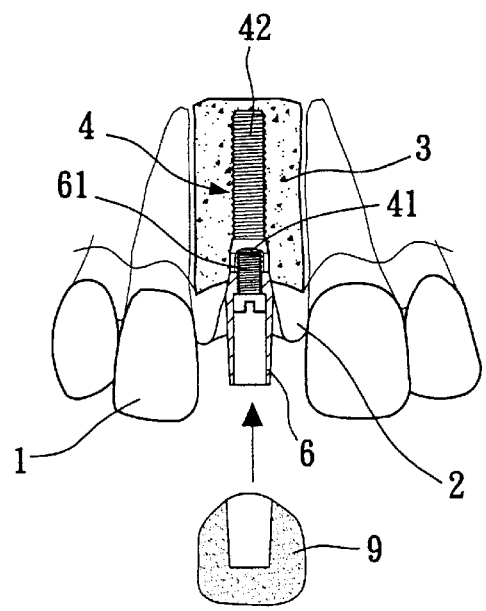
FIG. 6 shows a sixth step of mounting the conventional gum adjusting and shaping device for implanting an artificial tooth.
Figure 7:
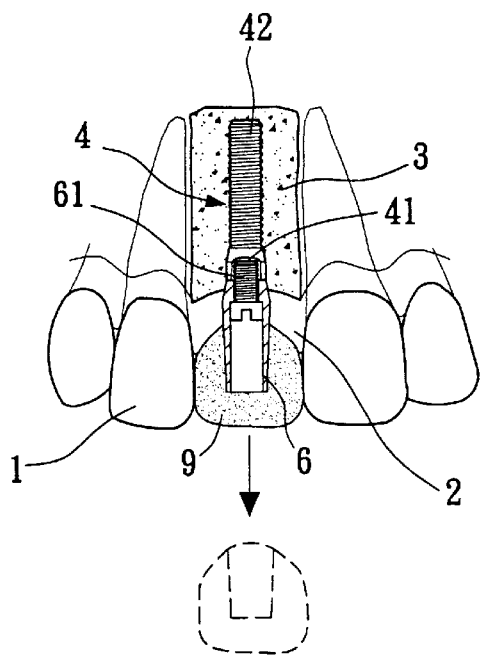
FIG. 7 shows a seventh step of mounting the conventional gum adjusting and shaping device for implanting an artificial tooth.
Figure 8:
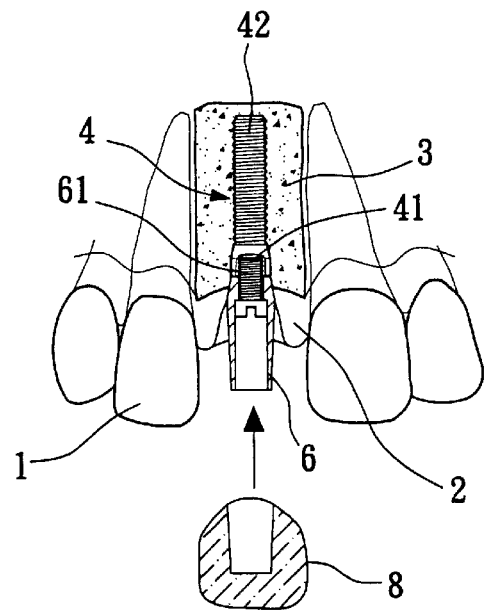
FIG. 8 shows an eighth step of mounting the conventional gum adjusting and shaping device for implanting an artificial tooth.
Figure 9:
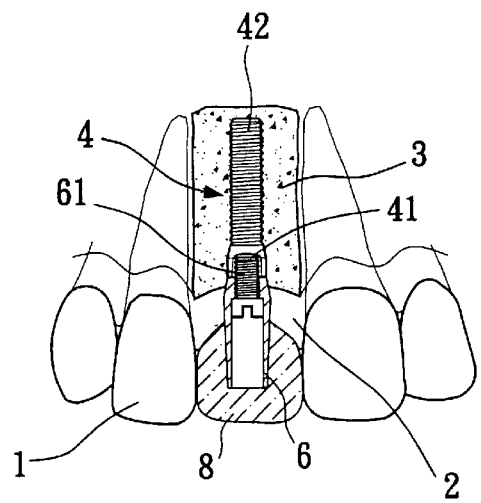
FIG. 9 shows a ninth step of mounting the conventional gum adjusting and shaping device for implanting an artificial tooth.
Figure 10:
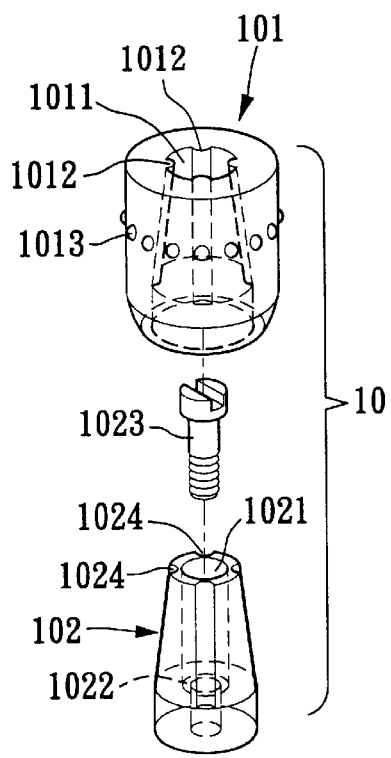
FIG. 10 is an exploded perspective view of a gum adjusting and shaping device according to the present invention.
Figure 11:
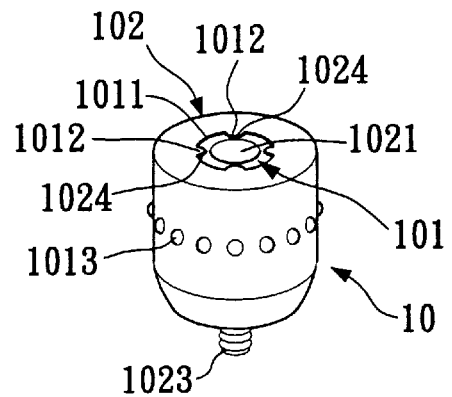
FIG. 11 is an assembled perspective view of FIG. 10.

Please refer to FIGS. 10 and 11. That are exploded and assembled perspective views, respectively, of a gum adjusting and shaping device 10 according to the present invention. As shown, the gum adjusting and shaping device 10 mainly includes an outer die 101, an abutment of implanted tooth 102 detachably fitted in the outer die 101, and a cap screw 1023 received in the abutment of implanted tooth 102.

The outer die 101 defines an inner space 1011 vertically extended through a full length of the outer die 101. At least two radially inward projected ribs 1012 are longitudinally and equally spaced along a peripheral wall of the inner space 1011. A circle of spaced dots 1013 are provided along an outer surface of the outer die 101. A rear end of the outer die 101 facing toward the gum is tapered shaped is tapered to form a truncated cone. The outer die 101 is made of an elastic material.

The abutment of implanted tooth 102 also defines an inner space 1021 vertically extended through a full length of the abutment of implanted tooth 102. A rear end of the inner space 1021 facing toward the gum is shaped to be reduced in diameter to form a stepped surface 1022 in the inner space 1021. The abutment of implanted tooth 102 has a length corresponding to that of the inner space 1011 of the outer die 101, and has an inclined outer peripheral wall on which at least two curve-bottomed grooves 1024 are longitudinally and equally spaced corresponding to the ribs 1012 in the inner space 1011 of the outer die 101. A rear portion of the abutment of implanted tooth 102 is shaped into a round tube that is adapted to tightly fit in the inner space 1011 of the outer die 101.

The cap screw 1023 is received in the inner space 1021 to abut on the stepped surface 1022 and project from the rear end of the inner space 1021, and thereby fixes the abutment of implanted tooth 102 to an artificial implant 4 previously implanted in a socket bone 3 to where the artificial tooth is to be implanted.

When the abutment of implanted tooth 102 is fitted in the inner space 1011 of the outer die 101, the curve-bottomed grooves 1024 are fitly engaged with the ribs 1012 to prevent undesired separation of the outer die 101 from the abutment of implanted tooth 102. FIGS. 12 to 18 illustrate steps for mounting the gum adjusting and shaping device 10 of the present invention for implanting an artificial tooth.

Figure 12:
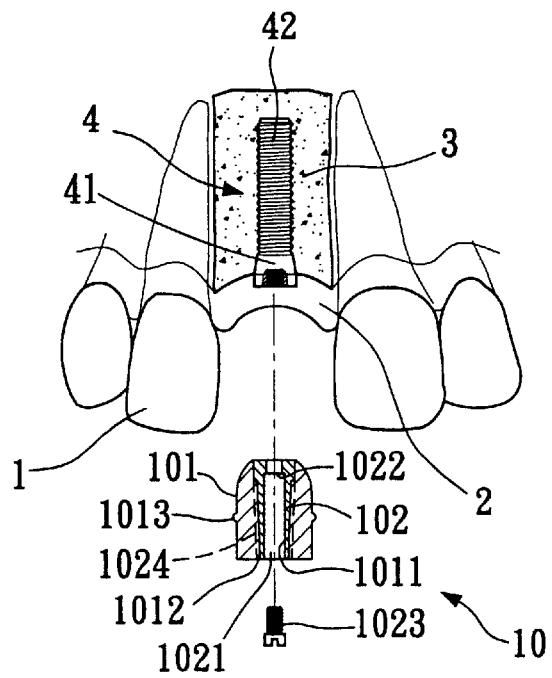
FIG. 12 shows a first step of mounting the gum adjusting and shaping device of the present invention for implanting an artificial tooth.

First, the gum 2 surrounding an empty socket of an extracted tooth 1 is incised to expose a part of the socket bone 3 thereof. A hole is drilled on the exposed socket bone 3 with a special drill for implanting an artificial implant 4 thereinto. The artificial implant 4 is provided at a head portion facing toward the hole at the exposed socket bone 3 with a screw cavity 41 that is helpful in subsequent steps of mounting the gum adjusting and shaping device 10. Then, the gum 2 is sutured, as shown in FIG. 12. Normally, the socket bone 3 would adapt itself to and unite with the artificial implant 4 after a short period of time.

Figure 13:
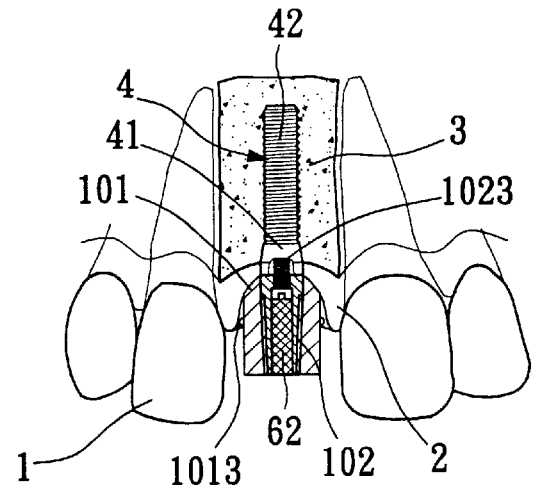
FIG. 13 shows a second step of mounting the gum adjusting and shaping device of the present invention for implanting an artificial tooth.
Figure 14:
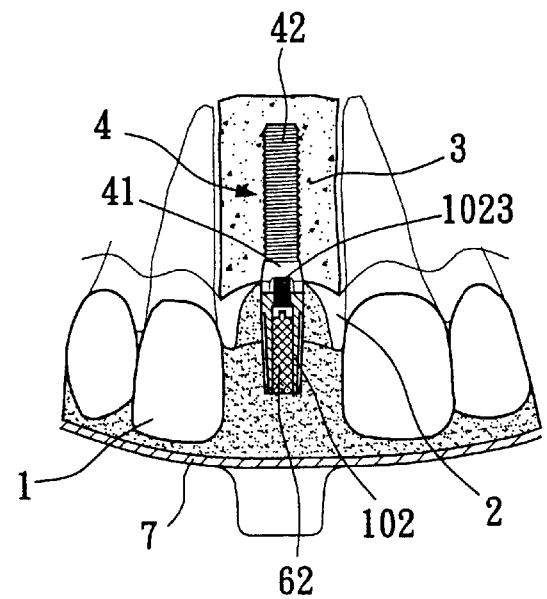
FIG. 14 shows a third step of mounting the gum adjusting and shaping device of the present invention for implanting an artificial tooth.

After the artificial implant 4 and the socket bone 3 are united, the healed gum 2 is incised again, and the entire gum adjusting and shaping device 10 is fixed to the artificial implant 4 implanted in the socket bone 3 by screwing the cap screw 1023 into the screw cavity 41. In this manner, the outer die 101 would expand the gum 2 open to form an enlarged cavity at the gum 2. This enlarged cavity enables subsequent formation of a tooth mold to deeply reach a root portion of the abutment of implanted tooth 102, as shown in FIG. 13. When the enlarged cavity at the gum 2 has become well shaped, the outer die 101 is removed from the cavity with a special clamp, and an impression tray with material 7 is used to take an accurate contour of the empty tooth socket, as shown in FIG. 14. Before taking the accurate contour of the empty tooth socket, filler 62 must be used to fill up the inner space 1021 of the abutment of implanted tooth 102, so as to ensure that a resultant artificial tooth 8 could be securely fitted on the abutment of implanted tooth 102. After the impression tray with material 7 is removed from the empty tooth socket, production of the desired artificial tooth 8 could be immediately started with a user-specified material.

Figure 15:
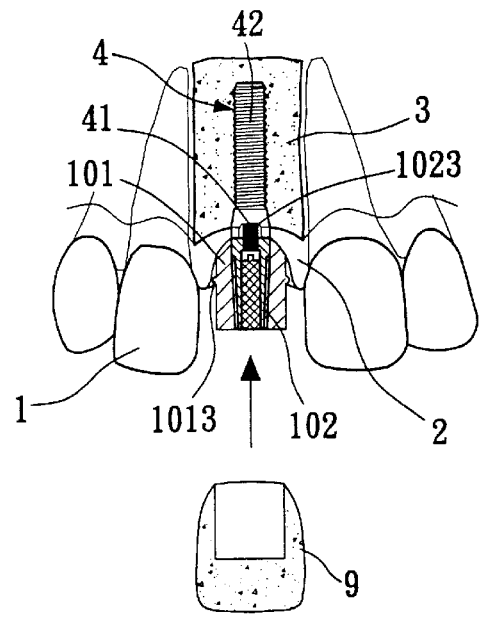
FIG. 15 shows a fourth step of mounting the gum adjusting and shaping device of the present invention for implanting an artificial tooth.
Figure 16:
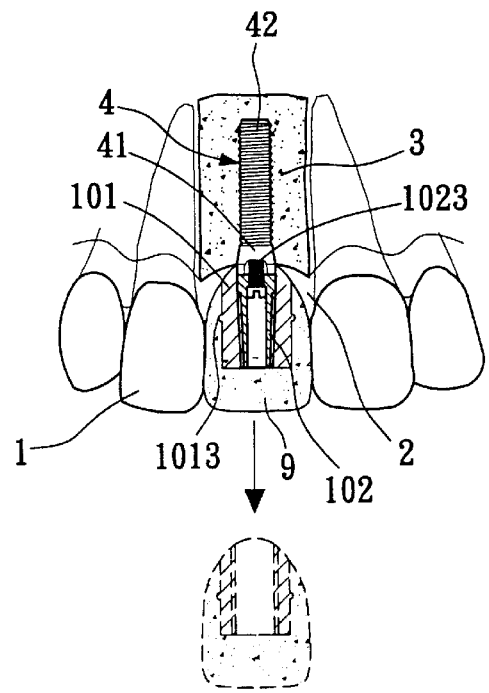
FIG. 16 shows a fifth step of mounting the gum adjusting and shaping device of the present invention for implanting an artificial tooth.
Figure 17:
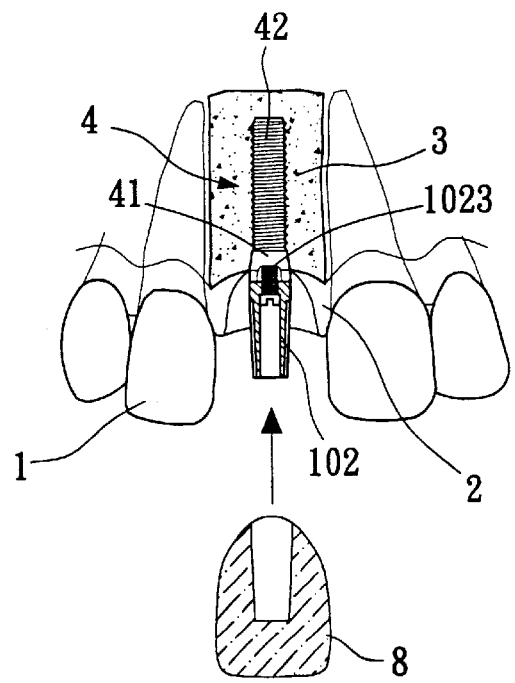
FIG. 17 shows a sixth step of mounting the gum adjusting and shaping device of the present invention for implanting an artificial tooth.
Figure 18:
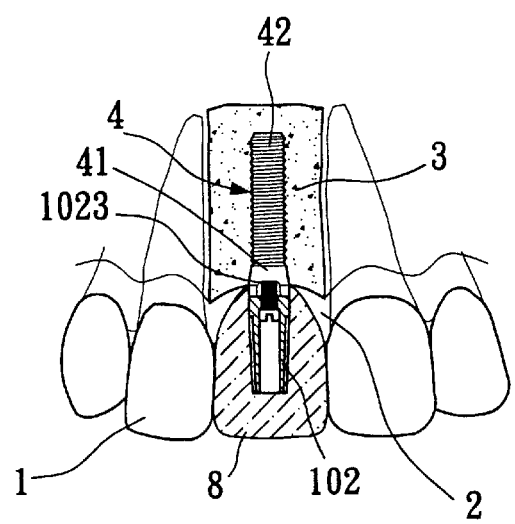
FIG. 18 shows a seventh step of mounting the gum adjusting and shaping device of the present invention for implanting an artificial tooth.

Since it takes a period of time to produce the desired artificial tooth 8, it is necessary to use a temporary artificial tooth 9 to substitute for the artificial tooth 8 during this period of time, as shown in FIGS. 15 and 16. Before the temporary artificial tooth 9 could be mounted, the outer die 101 must be attached to the abutment of implanted tooth 102 again for the temporary artificial tooth 9 to put thereon. The circle of dots 1013 on the outer die 101 enable a tight fit of the temporary artificial tooth 9 on the outer die 101 to maintain the enlarged cavity formed at the gum 2. When the desired artificial tooth 8 is completed, the temporary artificial tooth 9 along with the outer die 101 are removed from the abutment of implanted tooth 102, and the desired artificial tooth 8 is then fixed to the abutment of implanted tooth 102 by means of a bonding agent, as shown in FIGS. 17 and 18.

With the above-described arrangements, the gum adjusting and shaping device of the present invention is superior to the conventional structure due to the following advantages:

1. The step of mounting the gum-healing cap 5 is omitted to reduce the time required for tooth implantation.

2. The elastic outer die enables formation of an enlarged cavity at the gum around the root of the abutment of implanted tooth, and accordingly, subsequent formation of a tooth mold deeply reaching the root of the abutment of implanted tooth for producing a desired artificial tooth completely matching with neighboring teeth.

3. The outer die is made of an elastic material that is inexpensive and could be easily manufactured at largely reduced cost.

4. Since the gum-healing cap is omitted, the steps of mounting and dismounting the gum-healing caps to and from the artificial implant are saved.

What is claimed is:

1. A gum adjusting and shaping device, comprising:

an abutments of implanted tooth for connecting to an artificial implant previously implanted in a tooth socket bone above an extracted tooth; and an outer die for expanding and shaping an area of gum to where a desired artificial tooth is to be mounted;
said outer die being a short cylindrical member having an inner space vertically extended through a full length of said outer die, at least two radially inward projected ribs being longitudinally and equally spaced along a peripheral wall that defines the inner space, and a rear end of said outer die facing toward the gum to be shaped being tapered to form a truncated cone; and said abutments of implanted tooth having an inner space vertically extended through a full length thereof, a rear end of the inner space of said abutment facing toward the gum to be shaped being reduced in diameter to provide a stepped surface, against which a cap screw extended into the inner space of said abutment is abutted before projecting from a rear end of said abutments of implanted tooth to engage with the artificial implant; said abutments of implanted tooth having a length corresponding to a length of the inner space of said outer die, and having an inclined outer peripheral wall on which at least two curve-bottomed grooves are formed, the grooves being longitudinally and equally spaced corresponding to said ribs in the inner space of said outer die; and a rear portion of said abutments of implanted tooth being shaped into a round tube that is adapted to tightly fit in the inner space of said outer die.

2. The gum adjusting and shaping device as claimed in claim 1, wherein said outer die is made of an elastic material.

3. The gum adjusting and shaping device as claimed in claim 1, wherein said outer die has a circle of spaced dots provided along an outer surface thereof.

* * * * *